(12) United States Patent
Kitaoka et al.

(10) Patent No.: US 11,013,891 B2
(45) Date of Patent: May 25, 2021

(54) MEDICAL ELONGATED BODY

(71) Applicant: TERUMO KABUSHIKI KAISHA, Tokyo (JP)

(72) Inventors: Takashi Kitaoka, Kanagawa (JP); Yuuichi Tada, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 287 days.

(21) Appl. No.: 16/251,528

(22) Filed: Jan. 18, 2019

(65) Prior Publication Data

US 2019/0151615 A1 May 23, 2019

Related U.S. Application Data

(63) Continuation of application No. PCT/JP2017/026111, filed on Jul. 19, 2017.

(30) Foreign Application Priority Data

Jul. 20, 2016 (JP) .............................. JP2016-142312
Jul. 20, 2016 (JP) .............................. JP2016-142313

(51) Int. Cl.
*A61M 25/01* (2006.01)
*A61B 17/34* (2006.01)
(Continued)

(52) U.S. Cl.
CPC ..... *A61M 25/0138* (2013.01); *A61B 1/00071* (2013.01); *A61B 17/00234* (2013.01);
(Continued)

(58) Field of Classification Search
CPC .............. A61M 25/0138; A61M 25/00; A61M 25/0113; A61M 25/09; A61M 25/0043;
(Continued)

(56) References Cited

U.S. PATENT DOCUMENTS

| 6,053,922 A | 4/2000 | Edwards et al. |
| 2009/0099554 A1* | 4/2009 | Forster ...................... F16C 1/04 606/1 |

(Continued)

FOREIGN PATENT DOCUMENTS

| JP | 11-509752 A | 8/1999 |
| JP | 2009-540952 A | 11/2009 |

(Continued)

OTHER PUBLICATIONS

International Search Report (PCT/ISA/210) dated Oct. 17, 2017, by the Japan Patent Office as the International Searching Authority for International Application No. PCT/JP2017/026111.

(Continued)

*Primary Examiner* — Theodore J Stigell
*Assistant Examiner* — Daniel Moore
(74) *Attorney, Agent, or Firm* — Buchanan Ingersoll & Rooney PC

(57) ABSTRACT

A medical elongated body includes a tube shaped body provided with a spiral slit. The tube shaped body has a pair of opposing surfaces, on both sides of the slit, opposing surfaces have a first side and a second side, a first convex portion protrudes from the first side and a second convex portion protrudes from the second side, the first convex portion and the second convex portion are adjacent to each other in the circumferential direction of the tube shaped body, and base portions of the first convex portion and the second convex portion are located on a common first spiral.

18 Claims, 12 Drawing Sheets

(51) Int. Cl.
*A61B 17/00* (2006.01)
*A61M 25/00* (2006.01)
*A61B 17/221* (2006.01)
*A61B 1/00* (2006.01)
*A61B 17/16* (2006.01)
*A61M 25/09* (2006.01)
*A61B 17/22* (2006.01)
*A61B 1/005* (2006.01)

(52) U.S. Cl.
CPC ............ *A61B 17/16* (2013.01); *A61B 17/221* (2013.01); *A61B 17/34* (2013.01); *A61M 25/00* (2013.01); *A61M 25/0113* (2013.01); *A61M 25/09* (2013.01); *A61B 1/005* (2013.01); *A61B 2017/00309* (2013.01); *A61B 2017/2212* (2013.01); *A61B 2017/22079* (2013.01); *A61M 25/0043* (2013.01); *A61M 2025/09133* (2013.01)

(58) Field of Classification Search
CPC ........... A61M 2025/09133; A61M 2025/0059; A61M 25/0051; A61B 17/34; A61B 17/00234; A61B 17/221; A61B 1/00071; A61B 17/16; A61B 2017/22079; A61B 2017/2212; A61B 1/005; A61B 2017/00309
See application file for complete search history.

(56) References Cited

U.S. PATENT DOCUMENTS

| | | | |
|---|---|---|---|
| 2012/0116247 | A1 | 5/2012 | Wawrzyniak et al. |
| 2014/0005708 | A1* | 1/2014 | Shelton, IV ..... A61B 17/07207 606/170 |

FOREIGN PATENT DOCUMENTS

| | | |
|---|---|---|
| JP | 2014-504890 A | 2/2014 |
| JP | 2015-525611 A | 9/2015 |
| WO | 97/03611 A1 | 2/1997 |
| WO | 2014/174661 A1 | 10/2014 |

OTHER PUBLICATIONS

Written Opinion (PCT/ISA/237) dated Oct. 17, 2017, by the Japan Patent Office as the International Searching Authority for International Application No. PCT/JP2017/026111.

An English Translation of the International Search Report (Form PCT/ISA/210) and the Written Opinion of the International Searching Authority (Form PCT/ISA/237) dated Oct. 17, 2017, by the Japanese Patent Office in corresponding International Application No. PCT/JP2017/026111. (10 pages).

* cited by examiner

MEDICAL ELONGATED BODY

CROSS-REFERENCES TO RELATED APPLICATIONS

This application is a continuation of International Application No. PCT/JP2017/026111 filed on Jul. 19, 2017, and claims the benefit of Japanese Application No. 2016-142312 filed on Jul. 20, 2016 and Japanese Application No. 2016-142313 filed on Jul. 20, 2016, the entire content of each of which is incorporated herein by reference.

FIELD

The present invention relates to a medical elongated body to be inserted into a biological lumen.

BACKGROUND DISCUSSION

Medical devices having tube shaped medical elongated bodies, such as those used in catheters and the like, typically require both high flexibility and the ability to transmit torque. These properties need to be maintained up to the distal end of the device in order to be able to adapt to the shape of a biological lumen within which it is used and to successfully reach a target site in the biological lumen. As a method of making such a tube shaped medical elongated body flexible, it is known to provide a spiral slit in a tube shaped body provided in the medical elongated body. However, in addition to increasing flexibility, providing a spiral slit in such a medical elongated body will also promote expansion and contraction in an axial direction. Furthermore, since the spiral can contract (i.e., the winding can become tight) and expand (i.e., the winding can become loose), twisting tends to occur in the medical elongated body, leading to deterioration in the torque transmission performance to the distal end. Accordingly, attempts have been made to reduce the twisting tendence of the medical elongated body caused by the spiral slit. For example, WO 2014/174661 discloses a medical elongated body provided with a convex portion on one side of a pair of opposing surfaces forming a spiral slit and a concave portion in which the convex portion is accommodated on the other side of the opposing surfaces. In such a medical elongated body, since the convex portion is accommodated in the concave portion, the convex portion is caught in the concave portion in a circumferential direction so that the occurrence of twisting can be suppressed.

SUMMARY

However, in the medical elongated body disclosed in WO 2014/174661, the provision of the convex portion and the concave portion results in a site where the stress concentrates, which may cause breakage. Moreover, when the above-described medical elongated body bends, the convex portion is partially or entirely released from the concave portion, so that it becomes difficult to suppress the twisting, and the torque transmission performance can thus deteriorate.

The present invention has been made to solve the above-described problems, and an object of the present invention is to provide a medical elongated body capable of improving torque transmission performance by suppressing twisting while maintaining high flexibility, and suppressing occurrence of breakage by dispersing stress.

A medical elongated body that achieves the above-described object includes a tube shaped body provided with a spiral slit, in which the tube shaped body has a pair of opposing surfaces on both sides of the slit, the opposing surfaces have a first side and a second side located opposite to the first side with the slit interposed therebetween, and a first convex portion protrudes from the first side and a second convex portion protrudes from the second side, the first convex portion and the second convex portion are adjacent to each other in a circumferential direction of the tube shaped body, and base portions of the first convex portion and the second convex portion are located on a common spiral.

The medical elongated body configured as described above can obtain high flexibility because the base portions of the first convex portion and the second convex portion are located on a common spiral. Moreover, the medical elongated body is provided with the first convex portion and the second convex portion adjacent to each other on the opposing surfaces, so that the rotation force can be dispersed and uniformly act on two first convex portions and second convex portions. Accordingly, in the medical elongated body, the torque transmission performance can be improved by suppressing the twisting and the occurrence of breakage can be suppressed by dispersing the stress.

DETAILED DESCRIPTION

Figure 1:
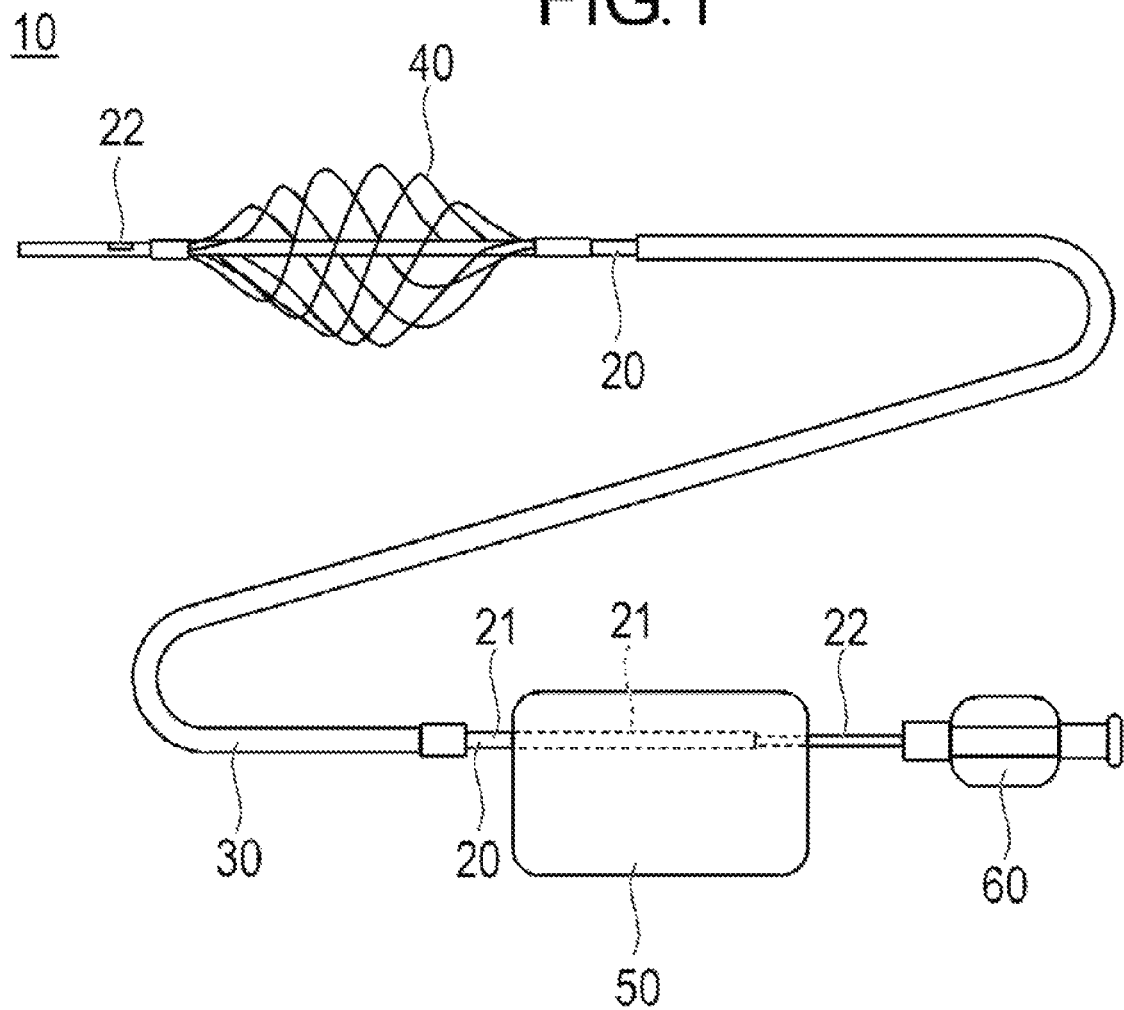
FIG. 1 is a plane view showing a medical elongated body according to an embodiment.
Figure 2:
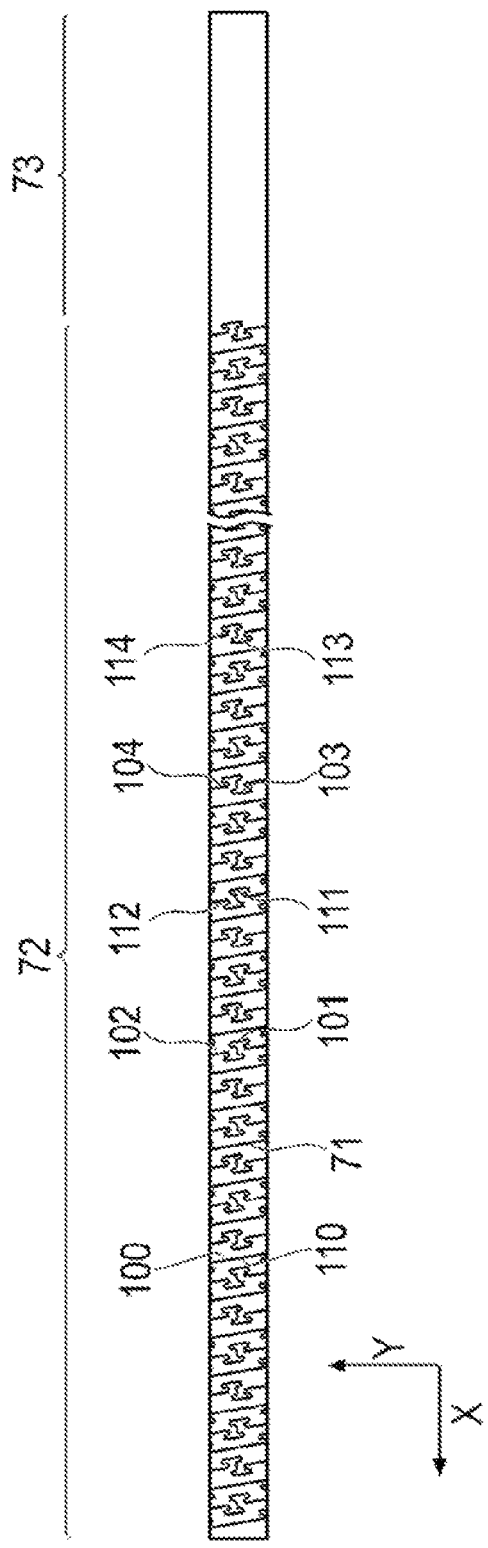
FIG. 2 is a plane view showing a tube shaped body.
Figure 3:
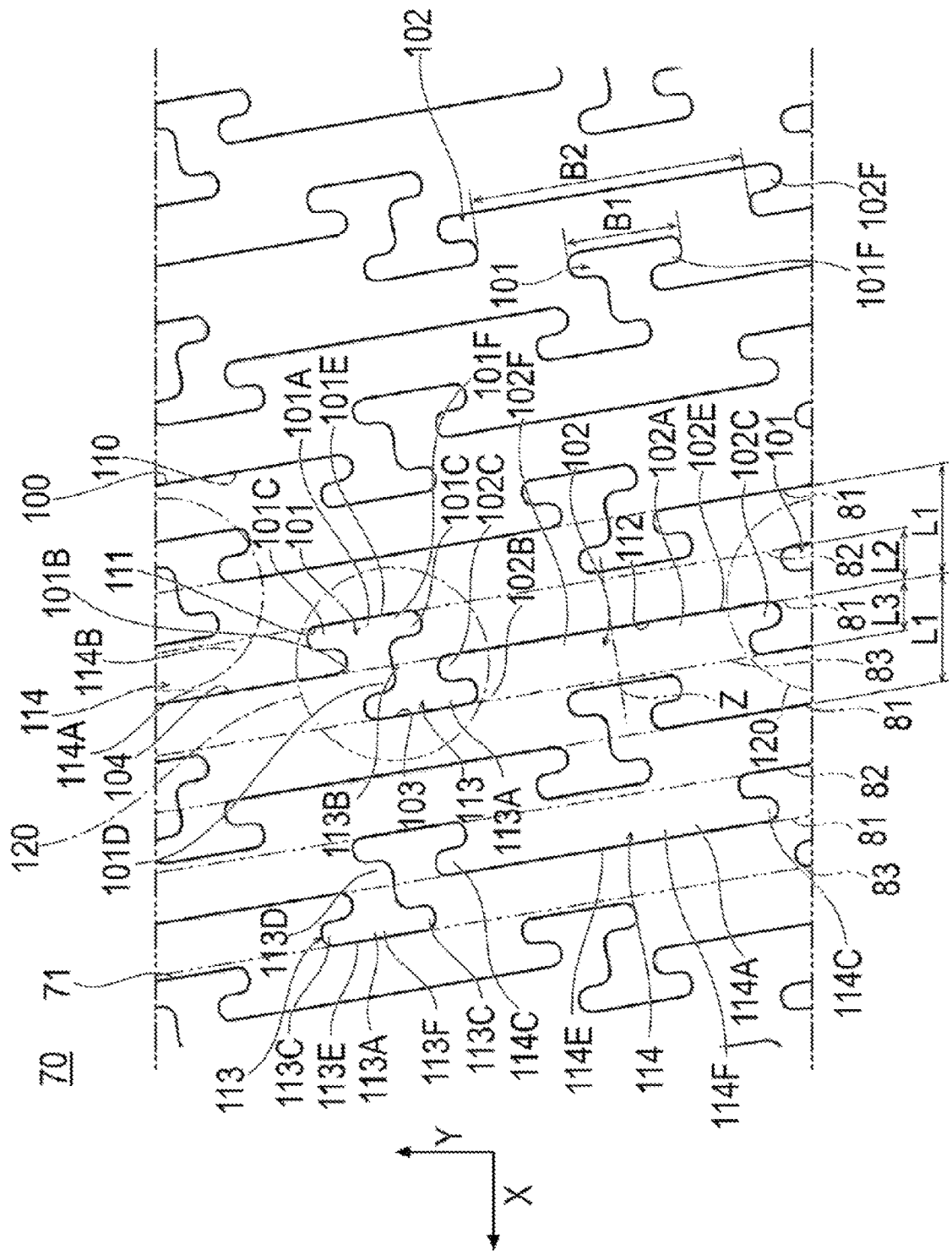
FIG. 3 is a developed view showing a portion of the tube shaped body in a circumferential direction.
Figure 4:
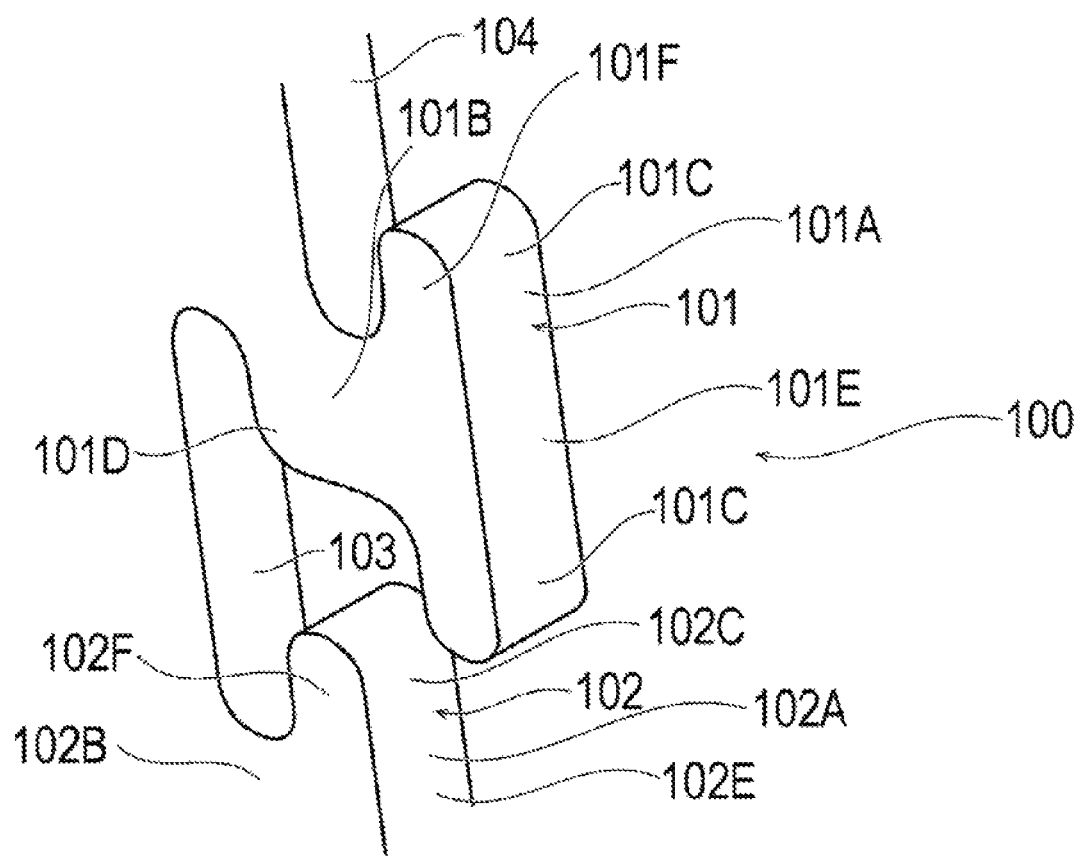
FIG. 4 is a perspective view showing a first side of opposing surfaces of the tube shaped body.
Figure 5:
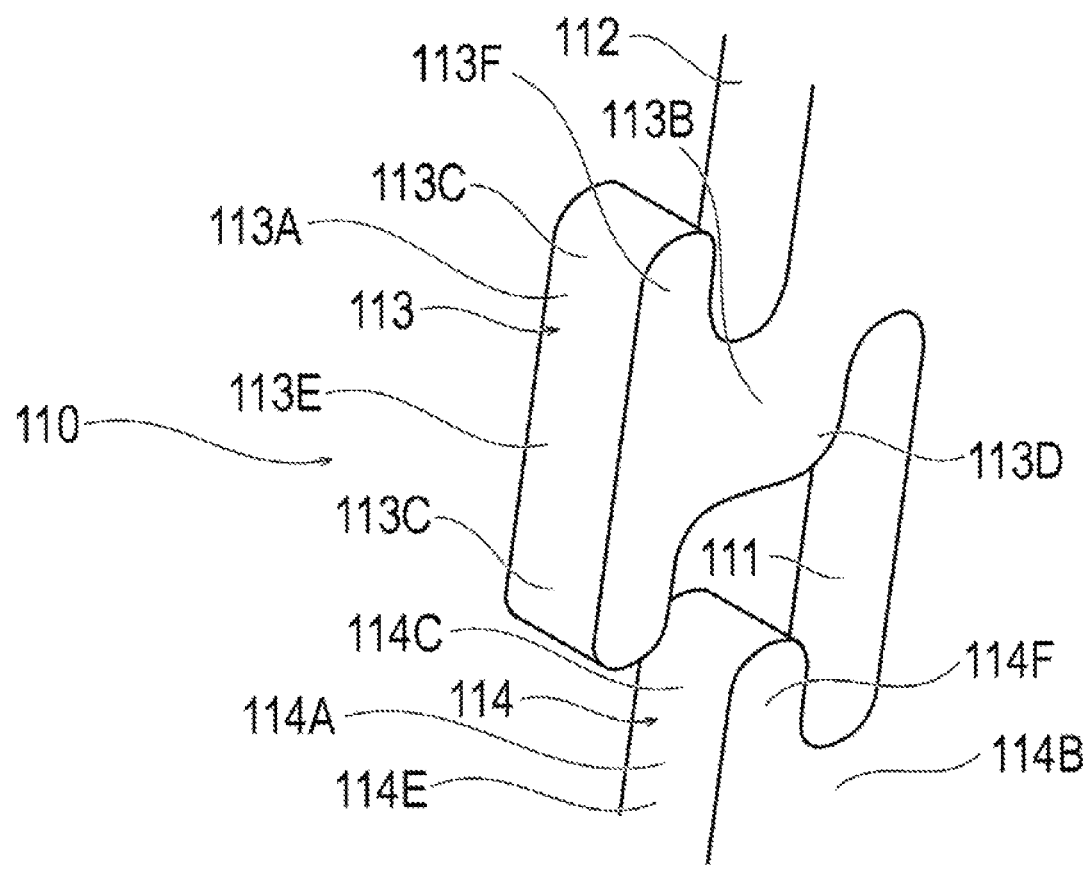
FIG. 5 is a perspective view showing a second side of the opposing surfaces of the tube shaped body.

Hereinafter, embodiments of the present invention will be described with reference to the drawings. Note that, dimension ratios in the drawings may be exaggerated and may differ from the actual ratios for convenience of description.

In a patient with deep vein thrombosis, a medical elongated body 10 according to the present embodiment is inserted into a blood vessel and used in a procedure for crushing and removing a thrombus. In the present specification, a side of the device inserted into a blood vessel is referred to as a "distal side", and a hand-side to be operated is referred to as a "proximal side".

The medical elongated body 10 includes, as shown in FIG. 1, an elongated shaft portion 20 which is rotationally driven, an outer sheath 30 which can accommodate the shaft portion 20, and a crushing portion 40 which is rotated by the shaft portion 20. The medical elongated body 10 further includes a rotationally driving portion 50 which has a driving source (for example, motor) for rotating the shaft portion 20 and a hub 60 which is provided at a proximal side end portion of the shaft portion 20. The crushing portion 40 is a plurality of elastically deformable wire rods. Note that, the configuration of the crushing portion 40 is not particularly limited as long as it can crush the substance in the lumen. The lumen includes blood vessels, arteries, veins, vessels and the like. The substance includes, but are not particularly limited to, a thrombus, a plaque, fibrous substances, calcified substances, fibrous blood vessels, calcified blood vessels, and the like.

The shaft portion 20 includes an outer tube shaft 21 rotationally driven by the rotationally driving portion 50 and an inner tube shaft 22 disposed on the inner side of the outer tube shaft 21 and to which the hub 60 is fixed at the proximal portion. The outer tube shaft 21 includes a tube shaped body 70 in which a spiral slit 71 is provided so as to transmit rotationally driving force while obtaining flexibility.

The tube shaped body 70 includes, as shown in FIGS. 2 to 6, a flexible portion 72 on a distal side in which the spiral slit 71 is provided and a high rigidity portion 73 on a proximal side in which the slit 71 is not formed. The slit 71 is formed by spiral slit processing using a technique such as laser processing.

The flexible portion 72 is provided with the slit 71 at a predetermined pitch L1. The slit 71 is a linear slit penetrating from an outer peripheral surface to an inner peripheral surface of the tube shaped body 70. The slit 71 is continuous so as to draw a spiral while curving so as to form a convex portion and a concave portion to be described later in the tube shaped body 70. The pitch L1 means a distance that the slit 71 moves in an axial direction X of the tube shaped body 70 by winding around 360 degrees in the circumferential direction. The flexible portion 72 of the tube shaped body 70 has a flexible structure easily bendable due to the reduced flexural rigidity by forming the slit 71. Note that, the tube shaped body 70 may be configured with a multiple spiral structure by providing a plurality of spiral slits. The flexible portion 72 has one belt portion 200 which is a belt shape plate member between the slits 71 aligned in the axial direction X (see FIG. 6). The belt portion 200 draws a spiral and constitutes the flexible portion 72. Note that, in a case where the tube shaped body 70 has the multiple spiral structure, the flexible portion is configured of a plurality of belt portions.

The slit 71 is configured by a pair of opposing surfaces 100 and 110 disposed opposite to each other. The opposing surface 100 (or opposing surface 110) is located on a first side of the pair of opposing surfaces 100 and 110, and the opposing surface 110 (or opposing surface 100) is located on a second side thereof. The first side of the opposing surfaces can be the proximal side, the distal side, or the circumferential direction side. The second side of the opposing surfaces is opposite to the first side. The opposing surface 100 is an end surface (first side) on the proximal side of the spiral structure body located between two slits 71 aligned in the axial direction. The opposing surface 100 is a surface connecting the inner peripheral surface and the outer peripheral surface of the tube shaped body 70. The opposing surface 100 extends in the circumferential direction along the spiral structure body located between the slits 71. The opposing surface 110 is an end surface (second side) on the distal side of the spiral structure body located between two slits 71 aligned in the axial direction. The opposing surface 110 is a surface connecting the inner peripheral surface and the outer peripheral surface of the tube shaped body 70. The opposing surface 110 extends in the circumferential direction along the spiral structure body located between the slits 71. The opposing surface 100 and the opposing surface 110 face each other with the slit 71 interposed therebetween. A plurality of first convex portions 101 and a plurality of third convex portions 102 protruding toward the proximal side are provided on the opposing surface 100 on the distal side. A plurality of first concave portions 111 into which the first convex portions 101 enter and a plurality of third concave portions 112 into which the third convex portions 102 enter are provided on the opposing surface 110 on the proximal side. The first convex portions 101 are caught in the first concave portions 111 so that the relative movement of the tube shaped body 70 in the axial direction X and the circumferential direction Y is restricted. The third convex portions 102 are caught in the third concave portions 112 so that the relative movement in the axial direction X and the circumferential direction Y is restricted.

The slit 71 can be located on three parallel first spirals 81, second spirals 82, or third spirals 83 by drawing a spiral while curving in the tube shaped body 70. Each of the first spiral 81, the second spiral 82, and the third spiral 83 draws a spiral at a constant pitch along the axial direction. Therefore, the first spiral 81, the second spiral 82, and the third spiral 83 have a constant spiral angle with respect to the axis of the tube shaped body 70. Top portions 102A of the third convex portions 102 and base portions 101B of the first convex portions 101 are located on the first spiral 81. Top portions 101A of the first convex portions 101 are located on the second spiral 82. Base portions 102B of the third convex portions 102 are located on the third spiral 83. By locating the slit 71 on the plurality of spirals (first spiral 81, second spiral 82, or third spiral 83), the tube shaped body 70 easily bends with each of the spirals as a joint, and becomes flexible.

Moreover, a linear first end surface 101E is provided at the top portions 101A of the first convex portions 101. A plurality of the first end surfaces 101E aligned in the circumferential direction Y are located on the second spiral 82. Moreover, a linear third end surface 102E is provided at the top portions 102A of the third convex portions 102. A plurality of the third end surfaces 102E aligned in the circumferential direction Y are located on the first spiral 81.

Each of the first convex portions 101 has a first wide portion 101F having a width wider on the protruding side (proximal side). The first wide portion 101F has two first overhanging portions 101C protruding toward both sides of the extending direction (circumferential direction Y) of the spiral. Moreover, each of the first convex portions 101 has a stepped portion 101D in which the width in the circumferential direction changes stepwise between one of the first overhanging portions 101C and the third spiral 83. Moreover, each of the third convex portions 102 has a third wide portion 102F having a width wider on the protruding side (proximal side). The third wide portion 102F has two third overhanging portions 102C protruding toward both sides of the extending direction (circumferential direction Y) of the spiral. The protruding sides of the first convex portions 101 and the third convex portions 102 may be the distal side or the circumferential direction side.

A maximum width B1 of the first convex portions 101 in the circumferential direction Y is shorter than a minimum width B2 of the third convex portions 102 in the circumferential direction Y. Then, the third convex portions 102 are disposed so as to overlap the first convex portions 101 in the axial direction X on the slit 71 adjacent to the protruding side of the first convex portions 101. Accordingly, the third convex portions 102 having a long length in the circumferential direction Y are located on the protruding side of the first convex portions 101. The maximum width B1 of the first convex portions 101 is located within the range of the minimum width B2 of the third convex portions 102 adjacent to the protruding side of the first convex portions 101 in the circumferential direction Y. Therefore, it is possible to suppress an interval between the slit 71 and the slit 71 adjacent to each other in the axial direction X from being partially narrowed, and to suppress the occurrence of breakage. Moreover, since the interval between the slit 71 and the slit 71 can be suppressed from being partially narrowed in the tube shaped body 70, the easily bending position is not easily deviated in the circumferential direction Y, and the appropriate strength can be secured.

A plurality of second convex portions 113 and a plurality of fourth convex portions 114 protruding toward the distal side are on the opposing surface 110 on the proximal side. A plurality of second concave portions 103 into which the second convex portions 113 enter and a plurality of fourth concave portions 104 into which the fourth convex portions 114 enter are provided on the opposing surface 100 on the distal side. The second convex portions 113 are caught in the second concave portions 103 so that the relative movement in the axial direction X and the circumferential direction Y is restricted. The fourth convex portions 114 are caught in the fourth concave portions 104 so that the relative movement in the axial direction X and the circumferential direction Y is restricted.

Base portions 113B of the second convex portions 113 and top portions 114A of the fourth convex portions 114 are located on the first spiral 81. A linear fourth end surface 114E is provided at the top portions 114A. Top portions 113A of the second convex portions 113 are located on the third spiral 83. A linear second end surface 113E is provided at the top portions 113A. Base portions 114B of the fourth convex portions 114 are located on the second spiral 82.

Each of the second convex portions 113 has a second wide portion 113F having a width wider on the protruding side (distal side). The second wide portion 113F has two second overhanging portions 113C protruding toward both sides of the extending direction (circumferential direction Y) of the spiral. Moreover, each of the second convex portions 113 has a stepped portion 113D in which the width in the circumferential direction changes stepwise between one of the second overhanging portions 113C. Moreover, each of the fourth convex portions 114 has a fourth wide portion 114F having a width wider on the protruding side (distal side). The fourth wide portion 114F has two fourth overhanging portions 114C protruding toward both sides of the extending direction (circumferential direction Y) of the spiral.

The first spiral 81 is a spiral (basic spiral) having the highest ratio on which the slit 71 is located. The location of the basic spiral having the highest ratio on which the slit 71 is located makes it possible to minimize the deviation in directionality with respect to the flexibility. The first spiral 81 is interposed between the second spiral 82 and the third spiral 83. A distance L2 between the first spiral 81 and the second spiral 82 in the axial direction X is equal to a distance L3 between the first spiral 81 and the third spiral 83 in the axial direction X. Note that, the distance L2 and the distance L3 may be different. It is preferable that the distance L2 and the distance L3 are equal to or less than half the pitch L1 of the first spiral 81 (basic spiral), but are not limited thereto. If the distance L2 and the distance L3 are equal to or less than half the pitch L1 of the basic spiral, the possibility of generation of a site where the interval between two slits 71 aligned in the axial direction X becomes excessively narrow is suppressed, and the width of the material between the two slits 71 can be maintained. Thereby, the appropriate strength can be secured in the tube shaped body 70. Moreover, it is preferable that the distance L2 and the distance L3 are not excessively short and a certain length is secured so that the strength of the first convex portions 101, the third convex portions 102, the second convex portions 113, and the fourth convex portions 114 can be secured. The pitch L1 is not particularly limited, but is, for example, 0.5 mm to 2.5 mm. The distance L2 and the distance L3 are not particularly limited, but are, for example, 0.25 mm to 1.25 mm.

A set of two of the first convex portions 101 and one of the third convex portions 102 are alternately disposed side by side along the spiral on the opposing surface 100 on the distal side. Moreover, a set of two of the second convex portions 113 and one of the fourth convex portions 114 are alternately disposed side by side along the spiral on the opposing surface 110 on the proximal side.

The first convex portions 101 on the opposing surface 100 on the distal side and the second convex portions 113 on the opposing surface 110 on the proximal side adjacent to each other are disposed in pairs in the circumferential direction Y. A convex portion group 120 configured of the first convex portions 101 and second convex portions 113 adjacent to each other is provided every 240 degrees along the basic spiral in the circumferential direction Y. The disposition of the first convex portions 101 and the second convex portions 113 is switched in the circumferential direction Y in the convex portion groups 120 adjacent to each other in the circumferential direction Y. Therefore, two convex portion groups 120 adjacent to each other in the circumferential direction Y are located at the center of the two convex portion groups 120 and line symmetrical with respect to an orthogonal line Z orthogonal to the spiral in the developed view.

Moreover, the adjacent first convex portions 101 and second convex portions 113 of each convex portion group 120 are, in a developed view, in a point symmetric shape with respect to a point located in a vicinity of the stepped portion 101D. That is, the first convex portions 101 and the second convex portions 113 have the same size and the shape, but differ only in orientation. Therefore, the second convex portions 113 have the same configuration with the first convex portions 101 but differ in orientation. Note that, having the same size means that the dimensions are the same. Moreover, having the same shape means that the shapes are in a similar relationship in a developed view.

Figure 6:
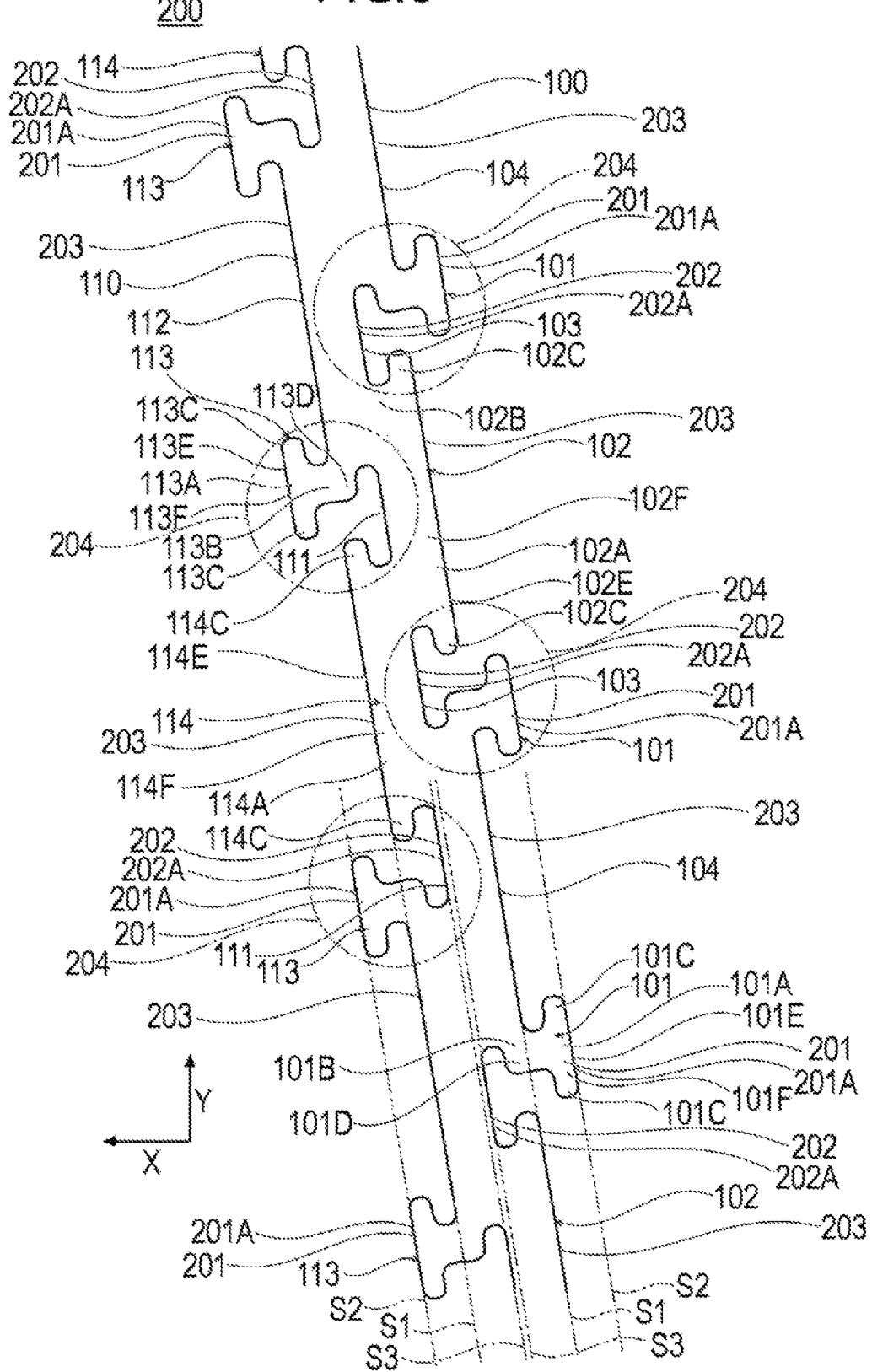
FIG. 6 is a developed view showing a portion of a belt portion of the tube shaped body continuously in the circumferential direction.

The convex portion group 120 is located every 240 degrees along the first spiral 81 (basic spiral) in the circumferential direction Y. Accordingly, the convex portion group 120 is not aligned along the axial direction X at the two slits 71 adjacent to each other in the axial direction X by being wound. Since the convex portion group 120 is located every 240 degrees in the circumferential direction Y, the convex portion group 120 is aligned in the axial direction X while interposing one slit 71 therebetween. The disposition of the first convex portions 101 and the second convex portions 113 is reversed in the circumferential direction Y in the two convex portion groups 120 aligned in the axial direction X with one slit 71 interposed therebetween. In other words, as illustrated in FIG. 6, for two convex portion groups 120 which are aligned with respect to the axial direction X and are adjacent with respect to the circumferential direction Y, the order of the first convex portion 101 and the second convex portion 113 in the circumferential direction Y within one group is opposite from the order of the first convex portion 101 and the second convex portion 113 in the circumferential direction Y within the other group.

The constituent material of the tube shaped body 70 is preferably a material with relatively high rigidity, and for example, metals such as Ni—Ti, brass, SUS, and aluminum are preferably used. Note that, as long as the material has relatively high rigidity, the constituent material of the tube shaped body 70 is not particularly limited, and for example, it may be a resin such as polyimide, vinyl chloride, and polycarbonate.

The dimension of the tube shaped body 70 is not particularly limited. For example, the tube shaped body 70 has an outer diameter of approximately 0.5 mm to 3.5 mm, a thickness of approximately 10 μm to 500 μm, and a length of approximately 100 mm to 5,000 mm.

A gap (separated distance between opposing surface 100 and opposing surface 110) of the slit 71 is not particularly limited, but is, for example, approximately 0.01 mm to 0.05 mm.

Next, a method of using the medical elongated body 10 according to the present embodiment will be described with a case of crushing and aspirating a substance in a vein as an example.

When using the medical elongated body 10 of the present embodiment, the medical elongated body 10 in a state in which a distal portion of the shaft portion 20 including the crushing portion 40 is accommodated in the outer sheath 30 is prepared. The crushing portion 40 is elastically deformed and contracted in the outer sheath 30.

Next, a guide wire (not shown) is inserted into the blood vessel, and the medical elongated body 10 reaches the proximal side of the substance with the guide wire as a guide. Thereafter, when the outer sheath 30 is moved to the proximal side with respect to the shaft portion 20, the crushing portion 40 is exposed to the outside of the outer sheath 30 and expands by its own elastic force.

Next, when the shaft portion 20 is rotated by the rotationally driving portion 50 in a state where the crushing portion 40 is advanced to the vicinity of the substance, the crushing portion 40 also rotates accordingly. When the crushing portion 40 is moved in the blood vessel in this state, the crushing portion 40 comes into contact with the substance, and the crushing portion 40 crushes the substance stuck in the blood vessel. Although the rotation of the crushing portion 40 is a reciprocating rotation, it may be continuously rotated in one direction.

Next, a syringe is interlocked with the hub 60 and a plunger is pulled to set the hollow inside portion of the shaft portion 20 to a negative pressure condition. Thereby, the crushed substance floating in the blood vessel can be aspirated and discharged to the outside of the blood vessel from an opening portion 23 located at the distal portion of the shaft portion 20. After the aspiration of the substance is completed, the rotationally driving portion 50 is operated to stop the rotation. Thereafter, the crushing portion 40 is accommodated in the outer sheath 30 and contracted, the medical elongated body 10 is removed from the blood vessel, and the procedure is completed.

Note that, it is possible to provide a side hole at the hand-side portion of the outer sheath 30, and to aspirate the substance from a distal end of the outer sheath 30 by interlocking the syringe to the side hole. Moreover, after crushing the substance, it is also possible to pull out the crushing portion 40 and the shaft portion 20 from the outer sheath 30, and to aspirate the substance by interlocking the syringe with the hub of the outer sheath 30.

As described above, the medical elongated body 10 according to the embodiment has the tube shaped body 70 provided with the spiral slit 71, the tube shaped body 70 has the pair of opposing surfaces 100 and 110 on both sides of the slit 71, the opposing surfaces have a first side and a second side located opposite to the first side with the slit 71 interposed therebetween, the first convex portions 101 protrude from the first side and the second convex portions 113 protrude from the second side, the first convex portions 101 and the second convex portions 113 are adjacent to each other in the circumferential direction of the tube shaped body 70, and the base portions 101B and 113B of the first convex portions 101 and the second convex portions 113 are located on the common first spiral 81 (spiral). The first spiral 81 is a spiral (basic spiral) having the highest ratio in which the slit 71 is located. The first spiral 81 has a constant spiral angle with respect to the axis of the tube shaped body 70. Note that, the first side of the opposing surfaces can be the proximal side, the distal side, or the circumferential direction side. The second side of the opposing surfaces is opposite to the first side. The medical elongated body 10 configured as described above has high flexibility because the base portions 101B and 113B of the first convex portions 101 and the second convex portions 113 are located on the common first spiral 81. Moreover, on the opposing surfaces 100 and 110, by providing the first convex portions 101 and the second convex portions 113 adjacent to each other, the rotation force of the medical elongated body 10 is dispersed and uniformly acts on two of the first convex portions 101 and the second convex portions 113. Accordingly, in the medical elongated body 10, the torque transmission performance can be improved by suppressing the twisting and the occurrence of breakage can be suppressed by dispersing the stress. In particular, since the tube shaped body 70 is a member for rotating and transmitting the rotation force, the operability can be improved by suppressing the twisting. Moreover, by improving the torque transmission capability, in a case where the crushing portion 40 receives excessive resistance at the time of crushing, the resistance is effectively transmitted to the proximal side and the medical elongated body 10 can be urgently stopped.

In the embodiment, the first convex portions 101 and the second convex portions 113 adjacent to each other in the circumferential direction are in a point symmetric shape in a circumferential developed view. Thereby, since the rotation force of the medical elongated body 10 is dispersed in the first convex portions 101 and the second convex portions 113 in a well-balanced manner, the torque transmission performance is improved, and the occurrence of the breakage can be further suppressed.

In the embodiment, the first convex portions 101 and the second convex portions 113 have widths wider on the protruding side in the circumferential direction. Thereby, the first convex portions 101 are caught on the side of the opposing surface 110, and the second convex portions 113 are caught on the side of the opposing surface 100. Accordingly, the tube shaped body 70 is caught in both directions of the axial direction X and the circumferential direction Y so that the elongation and the twisting can be suppressed.

In the embodiment, in the convex portion group 120 including the first convex portions 101 and the second convex portions 113 adjacent to each other, the disposition of the first convex portions 101 and the second convex portions 113 is reversed in the circumferential direction with respect to the other the convex portion groups 120 disposed side by side in the circumferential direction. Thereby, it is possible to suppress the deviation in the disposition of the first convex portions 101 and the second convex portions 113, and reduce the deviation in the flexibility in the circumferential direction Y.

In the embodiment, the first convex portions 101 and the second convex portions 113 have widths stepwise wider in two or more steps toward the protruding direction. Thereby, the first convex portions 101 and the second convex portions 113 are easily caught by each other. Accordingly, the elongation and the twisting in the medical elongated body 10 can be further suppressed.

In the embodiment, the first end surface 101E on the protruding side of the first convex portions 101 and the second end surface 113E on the protruding side of the second convex portions 113 are parallel with the first spiral 81 (basic spiral) on which the base portions of the first convex portions 101 and the second convex portions 113 are commonly located. Thereby, the tube shaped body 70 can be easily bent not only at the first spiral 81, but also at the position of the first end surface 101E (the second spiral 82) and the position of the second end surface 113E (third spiral 83). Therefore, the flexibility of the tube shaped body 70 is increased and the operability is improved.

In the embodiment, the first convex portions 101 and the second convex portions 113 are disposed at a position different from the other the first convex portions 101 and the second convex portions 113 provided on the adjacent slit 71 in the axial direction X in the circumferential direction Y. Thereby, the first convex portions 101 and the second convex portions 113 are not disposed continuously in the axial direction X. Accordingly, in the tube shaped body 70, the flexibility is not easily deviated in the circumferential direction Y, the adjustment of the bending position is facilitated, and the operability is improved.

In the embodiment, the first side further has the third convex portions 102 protruding toward the second side, the first convex portions 101 have the first wide portion 101F protruding toward the second side and having a width wider on the protruding side, the third convex portions 102 have the third wide portion 102F protruding toward the second side and having a width wider on the protruding side, the second side of the opposing surfaces has the first concave portions 111 and the third concave portions 112 which accommodate the first convex portions 101 and the third convex portions 102 so as to surround therewith, and at least one of the size and the shape of the first convex portions 101 and the third convex portions 102 is different. Note that, the first side of the opposing surfaces can be the proximal side, the distal side, or the circumferential direction side. The second side of the opposing surfaces is opposite to the first side. Thereby, in the medical elongated body 10, the first wide portion 101F of the first convex portions 101 and the third wide portion 102F of the third convex portions 102 are caught in the first concave portions 111 and the third concave portions 112 with respect to both directions of the axial direction X and the circumferential direction Y. Accordingly, in the medical elongated body 10, the elongation in the axial direction X and the occurrence of twisting are suppressed and the torque transmission performance is improved. Moreover, since at least one of the size and shape of the first convex portions 101 and the third convex portions 102 is different, the deviation (anisotropy) of the shape is reduced, and the deviation in the flexibility in the circumferential direction Y can be reduced. In particular, since the tube shaped body 70 is a member for rotating and transmitting the rotation force, the anisotropy of the torque transmission performance by the circumferential direction can be suppressed as much as possible and the operability can be improved by maintaining the flexibility that is not deviated as much as possible in the circumferential direction. Note that, herein, a configuration in which the first convex portions 101 and the third convex portions 102 of the opposing surface 100 on the distal side are accommodated in the first concave portions 111 and the third concave portions 112 of the opposing surface 110 on the proximal side will be described. However, the same effect is also obtained in the configuration in which the second convex portions 113 and the fourth convex portions 114 of the opposing surface 110 on the proximal side are accommodated in the second concave portions 103 and the fourth concave portions 104 of the opposing surface 100 on the distal side. Moreover, by improving the torque transmission capability, in a case where the crushing portion 40 receives excessive resistance at the time of crushing, the resistance is effectively transmitted to the proximal side and the medical elongated body 10 can be urgently stopped so that the safety is improved. Note that, the first wide portion 101F may have the same shape and size with the third wide portion 102F or they may be different.

In the embodiment, the protruding direction end portions of the first convex portions 101 and the third convex portions 102 adjacent to each other in the circumferential direction Y are located on a different spiral wound around the tube shaped body 70. Thereby, the tube shaped body 70 can be bent at both the position of the protruding direction end portion of the first convex portions 101 and the position of the protruding direction end portion of the third convex portions 102, and the flexibility is increased.

In the embodiment, the first end surface 101E on the protruding side of the first convex portions 101 and the third end surface 102E on the protruding side of the third convex portions 102 are parallel with the third spiral 83 (spiral) wound in a spiral shape on which at least one of the base portions of the first convex portions 101 and the third convex portions 102 is located. Thereby, the resistance is reduced when the tube shaped body 70 is bent at the position of the first end surface 101E and the position of the third end surface 102E, the flexibility is increased, and the operability is improved.

In the embodiment, the second spiral 82 (spiral) on which a plurality of the first end surfaces 101E are aligned is disposed at a position different from the first spiral 81 (spiral) on which a plurality of the third end surfaces 102E are aligned. Thereby, the tube shaped body 70 can be bent at both the position of the first end surface 101E and the position of the third end surface 102E, and the flexibility is increased.

In the embodiment, the first convex portions 101 are disposed at a position different from the other first convex portions 101 provided on the adjacent slit 71 in the axial direction X in the circumferential direction Y. Thereby, since the first convex portions 101 are not disposed continuously in the axial direction X, in the tube shaped body 70, the flexibility is not easily deviated in the circumferential direction Y, the adjustment of the bending position is facilitated, and the operability is improved.

In the embodiment, the first convex portions 101 have a length shorter than the third convex portions 102 in the circumferential direction Y, and, on the slit 71 adjacent to the protruding side of the first convex portions 101, the third convex portions 102 are located so as to overlap the first convex portions 101 in the axial direction X. Thereby, the third convex portions 102 having a long length in the circumferential direction Y are located on the protruding side of the first convex portions 101, so that it is possible to suppress the interval between the two slits 71 adjacent to each other in the axial direction X from being partially narrowed. Therefore, in the tube shaped body 70, the easily bending position is not easily deviated in the circumferential direction Y, and appropriate strength can be secured.

In the embodiment, the maximum width B1 of the first convex portions 101 in the circumferential direction Y is shorter than the minimum width B2 of the third convex portions 102 in the circumferential direction Y and, on the slit 71 adjacent to the protruding side of the first convex portions 101, the third convex portions 102 are disposed so as to overlap the first convex portions 101 in the axial direction X. Thereby, the third convex portions 102 having a long length in the circumferential direction Y are located on the protruding side of the first convex portions 101, so that it is possible to suppress the interval between the slits 71 adjacent to each other in the axial direction X from being partially narrowed. Therefore, in the tube shaped body 70, the easily bending position is not easily deviated in the circumferential direction Y, and the appropriate strength can be secured.

In the embodiment, the first convex portions 101 and the third convex portions 102 adjacent to each other in the circumferential direction are disposed side by side in the circumferential direction Y along the slit 71 while the disposition of the first convex portions 101 and the third convex portions 102 in the circumferential direction Y is alternately switched. Thereby, in the tube shaped body 70, the easily bending position is not easily deviated in the circumferential direction Y, the adjustment of the bending position is facilitated, and the operability is improved.

Moreover, in the medical elongated body 10 according to the embodiment, as shown in FIG. 6, the medical elongated body 10 has the tube shaped body 70 in which the belt portion 200 which is a plate member extending in a spiral shape is provided, the belt portion 200 has the inner peripheral surface located on the inner surface of the tube shaped body 70, the outer peripheral surface located on the outer surface of the tube shaped body 70, and two side surfaces interlocking the inner peripheral surface and the outer peripheral surface, the side surfaces have a mountain shape 201, a valley shape 202, and a straight shape 203, the mountain shape 201 and the valley shape 202 are adjacent to each other, a plurality of convex and concave portions 204 including the mountain shape 201 and the valley shape 202 adjacent to each other are provided, and the straight shape 203 connects the convex and concave portions 204. In the medical elongated body 10 configured as described above, by providing the mountain shape 201 and the valley shape 202 adjacent to each other on a side surface of the belt portion 200, the rotation force acting on the medical elongated body 10 is dispersed and uniformly acts on two mountain shapes 201 (a mountain shape 201 and another mountain shape 201 accommodated in a valley shape 202 adjacent to the mountain shape 201). Accordingly, in the medical elongated body 10, the torque transmission performance can be improved by suppressing the twisting and the occurrence of breakage can be suppressed by dispersing the stress. In particular, since the tube shaped body 70 is a member for rotating and transmitting the rotation force, the operability can be improved by suppressing the twisting. Moreover, by improving the torque transmission capability, in a case where the crushing portion 40 receives excessive resistance at the time of crushing, the resistance is effectively transmitted to the proximal side and the medical elongated body 10 can be urgently stopped.

Moreover, in the mountain shape 201 and the valley shape 202, the width of the belt portion 200 in the extending direction is wider at a top portion side of the mountain or at the bottom side of the valley. Accordingly, the mountain shape 201 is caught in the valley shape 202 accommodating the mountain shape 201 in both directions of the axial direction X and the circumferential direction Y. Accordingly, in the medical elongated body 10, the elongation in the axial direction X and the occurrence of twisting are suppressed and the torque transmission performance is improved.

Moreover, the mountain shape 201 and the valley shape 202 are fitted to each other by disposing the belt portion 200 in a spiral shape. Accordingly, the mountain shape 201 is more likely to be caught in the valley shape 202 accommodating the mountain shape 201 in both directions of the axial direction X and the circumferential direction Y. Accordingly, in the medical elongated body 10, the elongation in the axial direction X and the occurrence of twisting are suppressed and the torque transmission performance is improved.

Moreover, the mountain shape 201 and the valley shape 202 have substantially the same shape. Accordingly, the mountain shape 201 can be well fitted to the valley shape 202. Therefore, the mountain shape 201 and the valley shape 202 are easily caught in both directions of the axial direction X and the circumferential direction Y. Accordingly, in the medical elongated body 10, the elongation in the axial direction X and the occurrence of twisting are suppressed and the torque transmission performance is improved.

Moreover, the mountain shape 201 has a top surface 201A and the valley shape 202 has a bottom 202A. In a circumferential developed view of the tube shaped body, a first line S1 on which the straight shape 203 is located, a second line S2 on which the top surface 201A is located, and a third line S3 on which the bottom 202A is located are different in position. Thereby, the tube shaped body 70 is likely to bend at the positions, the first line S1, the second line S2, and the third line S3, and the flexibility is increased. Note that, the first line S1 is provided at a position corresponding to the first spiral 81. The second line S2 is provided at a position corresponding to the second spiral 82. The third line S3 is provided at a position corresponding to the third spiral 83.

Figure 7:
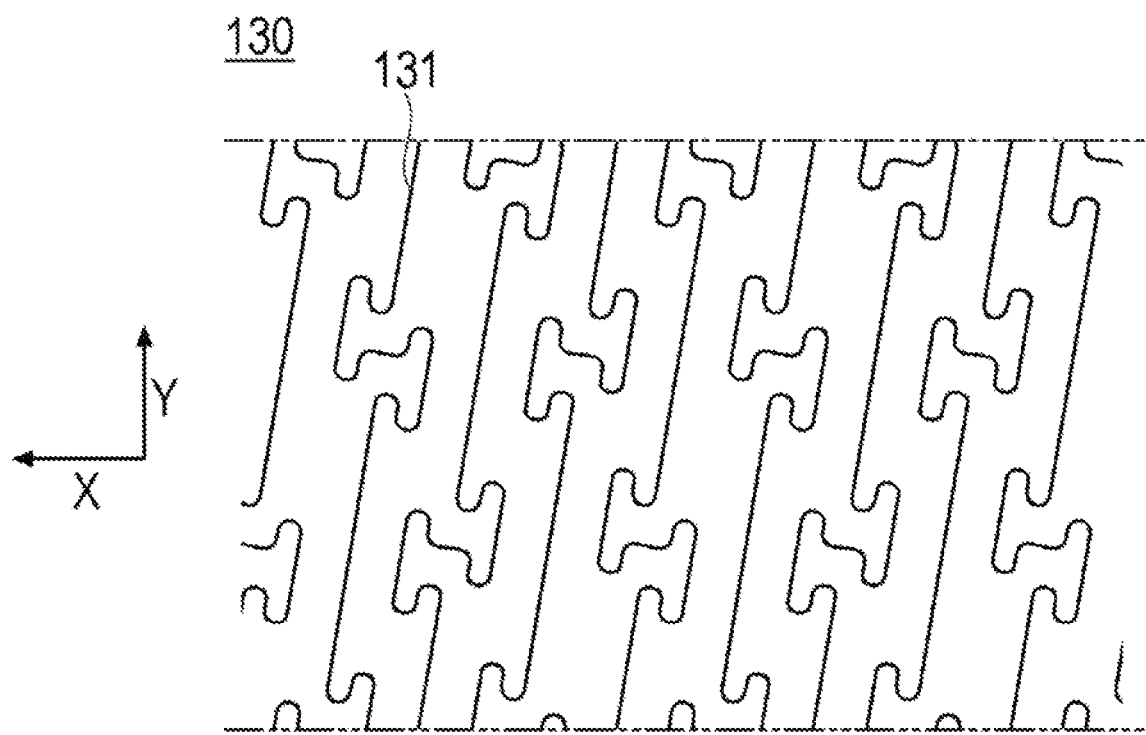
FIG. 7 is a developed view showing a portion of a first modification example of a tube shaped body in the circumferential direction.

Note that, the present invention is not limited only to the embodiments described above, and various modifications are possible by those skilled in the art within the technical idea of the present invention. For example, as shown in FIG. 7, in a tube shaped body 130 as a first modification example, the winding direction of a slit 131 may be opposite to that in the above-described embodiment.

Figure 8:
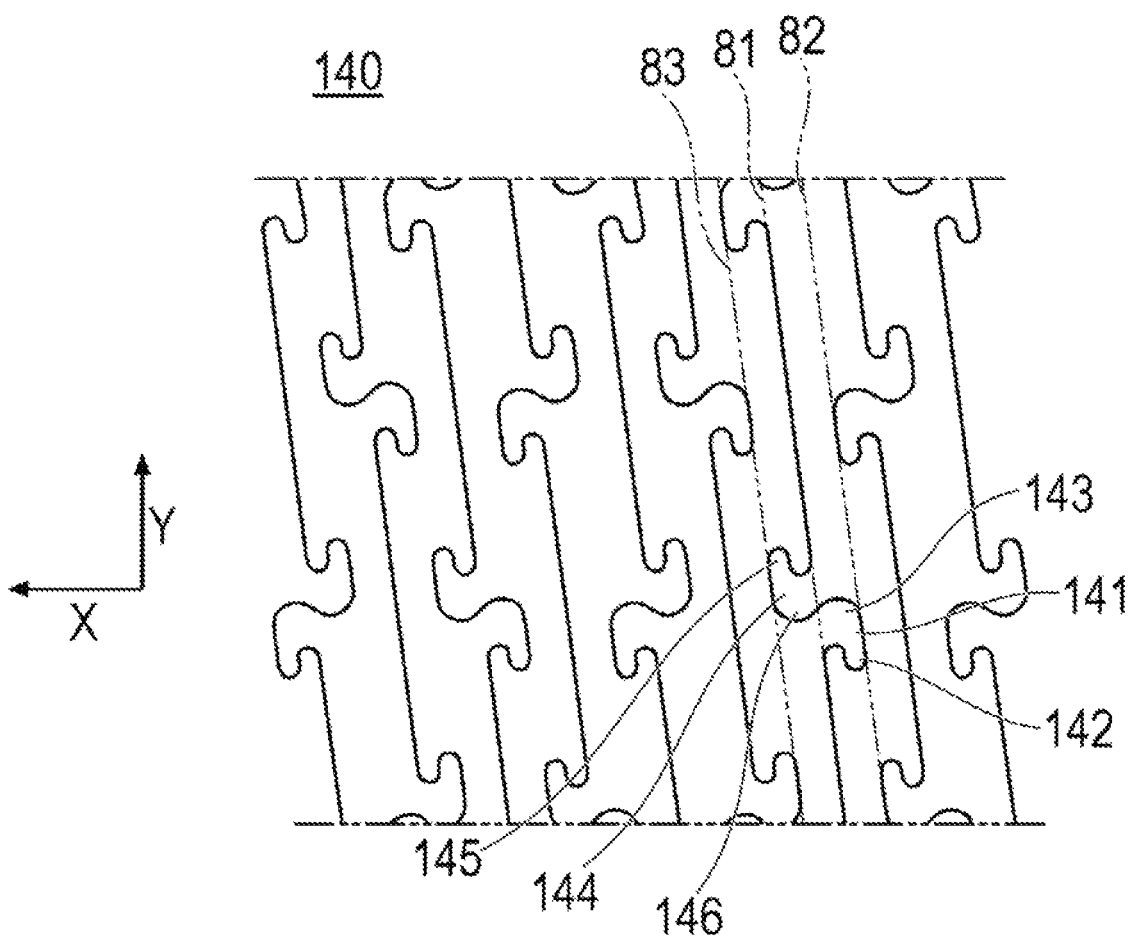
FIG. 8 is a developed view showing a portion of a second modification example of a tube shaped body in the circumferential direction.

Moreover, as shown in FIG. 8, in a tube shaped body 140 as a second modification example, the shape of two overhanging portions 142 and 143 provided in each first convex portion 141 is different from each other, and the shape of two overhanging portions 145 and 146 provided in a second convex portion 144 may be different from each other. Note that, the same reference numerals are attached to the parts having similar functions, and the description thereof will be omitted.

Figure 9:
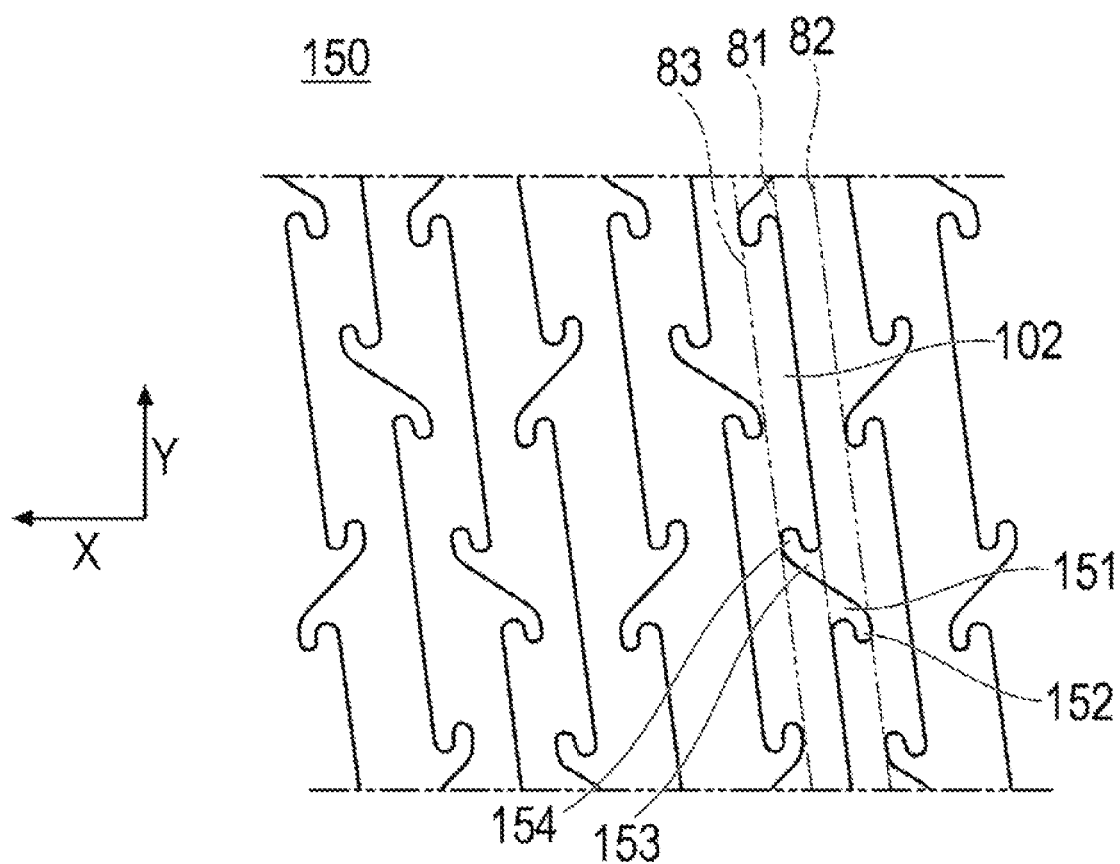
FIG. 9 is a developed view showing a portion of a third modification example of a tube shaped body in the circumferential direction.

Moreover, as shown in FIG. 9, in a tube shaped body 150 as a third modification example, each first convex portion 151 has one overhanging portion 152 instead of two, and a second convex portion 153 may have one overhanging portion 154.

Figure 10:
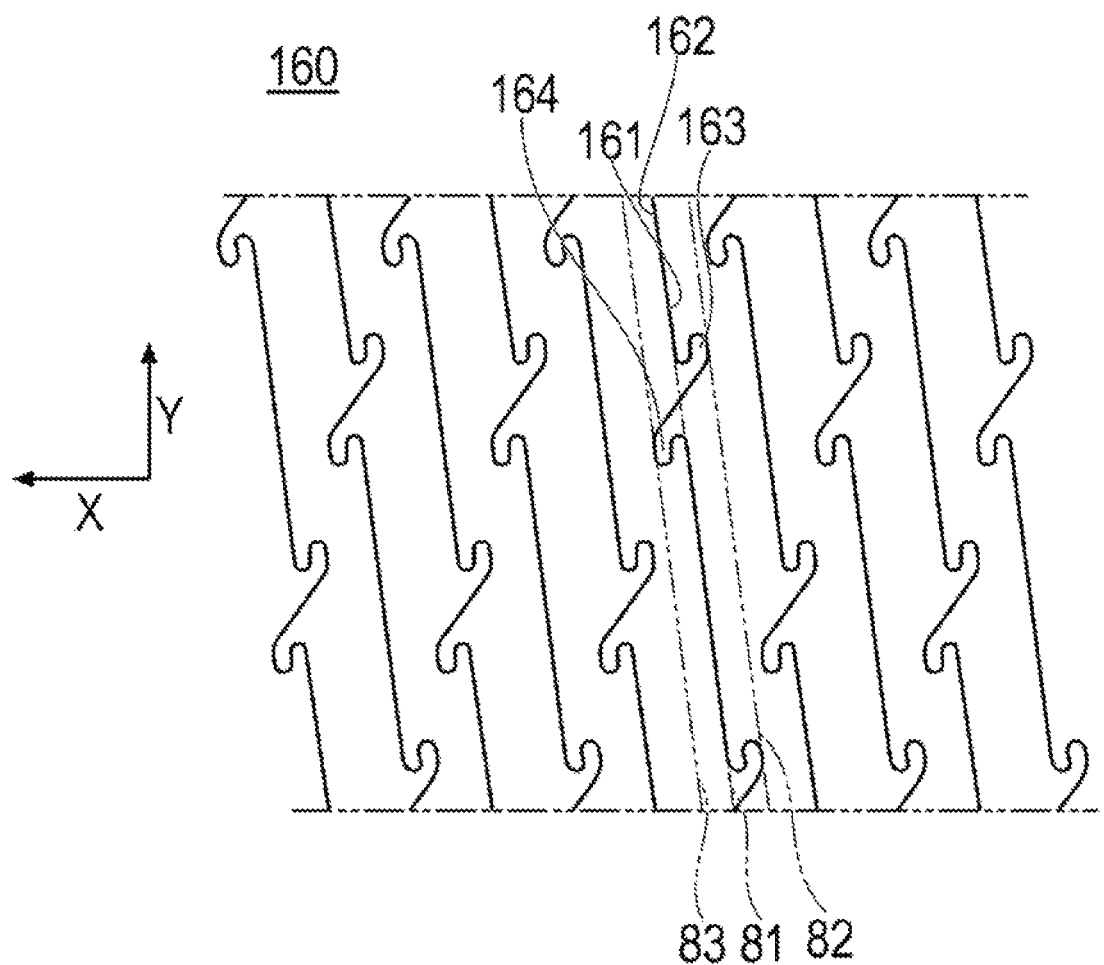
FIG. 10 is a developed view showing a portion of a fourth modification example of a tube shaped body in the circumferential direction.

Moreover, as shown in FIG. 10, in a tube shaped body 160 as a fourth modification example, disposition of a first convex portion 163 and a second convex portion 164 provided on opposing surfaces 161 and 162 facing each other and adjacent to each other may not always be reversed in the circumferential direction, and may always be the same. In other words, as illustrated in FIG. 10, for two groups of first and second convex portions 163 and 164 which are aligned with respect to the axial direction X and are adjacent with respect to the circumferential direction Y, the order of the first convex portion 163 and the second convex portion 164 in the circumferential direction Y within one group is the same as the order of the first convex portion 163 and the second convex portion 164 in the circumferential direction Y within the other group.

Figure 11:
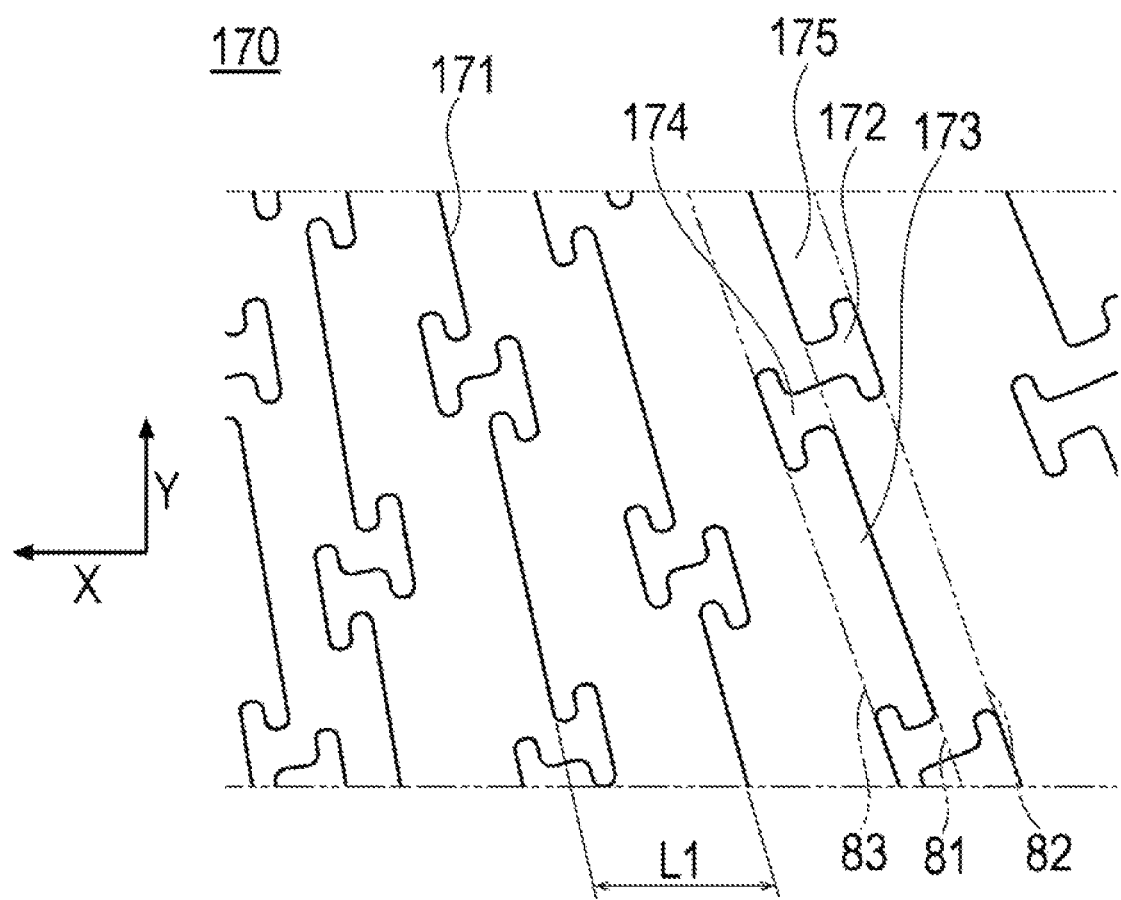
FIG. 11 is a developed view showing a portion of a fifth modification example of a tube shaped body in the circumferential direction.

Moreover, as shown in FIG. 11, in a tube shaped body 170 as a fifth modification example, the pitch L1 of a slit 171 may change along the axial direction X. For example, by gradually narrowing the pitch L1 of the slit 171 toward the distal side, it is possible to lower the flexural rigidity toward the distal side. Thereby, the tube shaped body 170 can secure sufficient pushing performance by a site on the proximal side having high flexural rigidity, can easily pass through a curved site of a biological lumen by a flexible site on the distal side, and can obtain high accessibility and operability at the same time. Similar to the slit 171, the first spiral 81, the second spiral 82, and the third spiral 83 gradually change along the axial direction. Moreover, the sizes and the shapes of a first convex portion 172, a second convex portion 174, a third convex portion 173, and a fourth convex portion 175 may be different depending on the position in the axial direction X. For example, in the proximal portion having the large pitch L1, since there is a room in the pitch L1, the first convex portion 172, the second convex portion 174, the third convex portion 173, and the fourth convex portion 175 can be enlarged. The pitch L1 of the slit 171 may change in an inclined manner. Thereby, the tube shaped body can obtain higher accessibility and operability, and the stress is not concentrated at one place, so that the occurrence of breakage and a kink can be reduced. Moreover, the pitch L1 of the slit may be shorter toward the proximal side. Moreover, the sizes and the shapes of the first convex portion, the second convex portion, the third convex portion, and the fourth convex portion may be smaller toward the proximal side.

Figure 12:
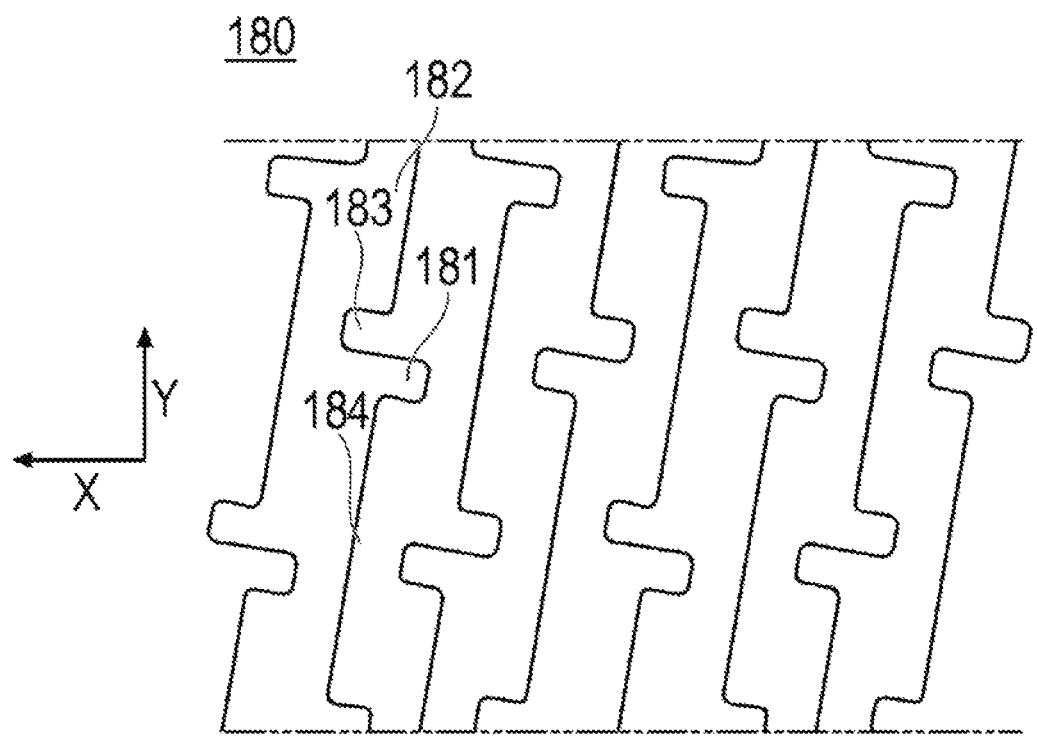
FIG. 12 is a developed view showing a portion of a sixth modification example of a tube shaped body in the circumferential direction.

Moreover, as shown in FIG. 12, in a tube shaped body 180 as a sixth modification example, a first convex portion 181, a third convex portion 182, a second convex portion 183, and a fourth convex portion 184 may be provided with respective constant widths, in contrast to widths that widen at the ends of the convex portions as in the previous embodiments.

Moreover, the medical elongated body 10 according to the present embodiment is a device for removing a thrombus in the vein, but is not particularly limited as long as it is a medical elongated body. For example, the medical elongated body may be an atherectomy device for scraping a calcified lesion area in an artery, catheters for other uses such as a microcatheter and an imaging catheter, a guide wire, and the like.

Moreover, the first convex portion and the third convex portion of the tube shaped body may be disposed with regularity, or may be randomly disposed. Thereby, the anisotropy in the circumferential direction in the flexural rigidity of the tube shaped body can be reduced. Note that, by disposing the first convex portion and the third convex portion of the tube shaped body with regularity, it is possible to systematically adjust the bending direction.

The detailed description above describes features and aspects of embodiments of a medical elongated body disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. A medical elongated body comprising:
   a tube shaped body provided with a spiral slit,
   wherein the tube shaped body has a pair of opposing surfaces on both sides of the slit,
   wherein the opposing surfaces have a first side and a second side located opposite to the first side with the slit interposed therebetween,
   wherein a first convex portion protrudes from the first side and a second convex portion protrudes from the second side, the first convex portion and the second convex portion are adjacent to each other in a circumferential direction of the tube shaped body, and base portions of the first convex portion and the second convex portion are located on a common spiral, and
   wherein the first convex portion and the second convex portion have widths stepwise wider in two or more steps toward a protruding direction.

2. The medical elongated body according to claim 1, wherein the first convex portion and the second convex portion adjacent to each other in the circumferential direction are in a point symmetric shape in a circumferential developed view.

3. The medical elongated body according to claim 1, wherein widths of the first convex portion and the second convex portion in the circumferential direction are wider on a protruding side.

4. The medical elongated body according to claim 1, wherein, in a convex portion group including the first convex portion and the second convex portion adjacent to each other, disposition of the first convex portion and the second convex portion is reversed in the circumferential direction with respect to other convex portion groups disposed side by side in the circumferential direction.

5. The medical elongated body according to claim 1, wherein the first side further includes a third convex portion protruding toward the second side,
   wherein the first convex portion protrudes toward the second side and has a first wide portion having a width wider on the protruding side,
   wherein the third convex portion protrudes toward the second side and has a third wide portion having a width wider on the protruding side,
   wherein the second side of the opposing surfaces has a concave portion surrounding and accommodating the first convex portion and the third convex portion, and
   wherein at least one of a size and a shape of the first convex portion and the third convex portion is different.

6. The medical elongated body according to claim 5, wherein protruding direction end portions of the first convex portion and the third convex portion adjacent to each other in the circumferential direction are located on a different spiral wound around the tube shaped body.

7. The medical elongated body according to claim 5, wherein a first end surface on the protruding side of the first convex portion and a third end surface on the protruding side of the third convex portion are parallel to a spiral wound around in a spiral shape on which at least one of base portions of the first convex portion and the third convex portion is located.

8. The medical elongated body according to claim 7, wherein a spiral on which a plurality of the first end surfaces are aligned is disposed at a position different from a spiral on which a plurality of the third end surfaces are aligned.

9. The medical elongated body according to claim 5, wherein the first convex portion is disposed at a position different from another first convex portion, provided on a slit adjacent in the axial direction, in the circumferential direction.

10. The medical elongated body according to claim 5, wherein the first convex portion has a length shorter than the third convex portion in the circumferential direction, and the third convex portion which overlaps the first convex portion in the axial direction is provided on a slit adjacent to the protruding side of the first convex portion.

11. The medical elongated body according to claim 10, wherein a maximum width of the first convex portion in the circumferential direction is shorter than a minimum width of the third convex portion in the circumferential direction, and a third convex portion is disposed on the slit adjacent to the protruding side of the first convex portion so as to overlap the first convex portion in the axial direction.

12. The medical elongated body according to claim 5, wherein the first convex portion and the third convex portion adjacent to each other in the circumferential direction are disposed side by side in the circumferential direction along the slit while the disposition of the first convex portion and the third convex portion in the circumferential direction is alternately switched.

13. A medical elongated body comprising:
a tube shaped body provided with a belt portion which is a plate member extending in a spiral shape,
wherein the belt portion has two side surfaces,
wherein each of the side surfaces has a mountain shape, a valley shape, and a straight shape,
wherein the mountain shape and the valley shape are adjacent to each other, a plurality of convex and concave portions including the mountain shape and the valley shape adjacent to each other are provided, and the straight shape connects the convex and concave portions, and
wherein the mountain shape and the valley shape, which are on opposite sides of a line defined by an extension of the straight shape, have substantially the same shape.

14. The medical elongated body according to claim 13, wherein each of the mountain shape and the valley shape has a width of the belt portion in the extending direction wider on a top portion side of the mountain or on a bottom side of the valley.

15. The medical elongated body according to claim 13, wherein the mountain shape and the valley shape are fitted to each other by disposing the belt portion in a spiral shape.

16. The medical elongated body according to claim 13, wherein the mountain shape has a top surface, and the valley shape has a bottom, and
wherein, in a circumferential developed view of the tube shaped body, a first line on which the straight shape is located, a second line on which the top surface is located, and a third line on which the bottom is located are different in position.

17. A medical elongated body comprising:
a tube shaped body provided with a spiral slit,
wherein the tube shaped body has a pair of opposing surfaces on both sides of the slit,
wherein the opposing surfaces have a first side and a second side located opposite to the first side with the slit interposed therebetween,
wherein a first convex portion protrudes from the first side and a second convex portion protrudes from the second side, the first convex portion and the second convex portion are adjacent to each other in a circumferential direction of the tube shaped body, and base portions of the first convex portion and the second convex portion are located on a common spiral, and
wherein, in a convex portion group including the first convex portion and the second convex portion adjacent to each other in the surface of the same side, disposition of the first convex portion and the second convex portion is reversed in the circumferential direction with respect to other convex portion groups disposed side by side in the circumferential direction.

18. A medical elongated body comprising:
a tube shaped body provided with a belt portion which is a plate member extending in a spiral shape,
wherein the belt portion has two side surfaces,
wherein each of the side surfaces has a mountain shape, a valley shape, and a straight shape,
wherein the mountain shape and the valley shape are adjacent to each other, a plurality of convex and concave portions including the mountain shape and the valley shape adjacent to each other are provided, and the straight shape connects the convex and concave portions, and
wherein the mountain shapes each have widths stepwise wider in two or more steps toward a protruding direction.

* * * * *